United States Patent [19]
Wu et al.

[11] Patent Number: 6,046,004
[45] Date of Patent: *Apr. 4, 2000

[54] SOLUTION HYBRIDIZATION OF NUCLEIC ACIDS WITH ANTISENSE PROBES HAVING MODIFIED BACKBONES

[75] Inventors: Yuan Min Wu; Eileen Xiao-Feng Nie, both of Thornhill, Canada

[73] Assignee: Lorne Park Research, Inc., Toronto, Canada

[*] Notice: This patent is subject to a terminal disclaimer.

[21] Appl. No.: 09/083,410

[22] Filed: May 22, 1998

Related U.S. Application Data

[63] Continuation-in-part of application No. 08/807,901, Feb. 27, 1997, abandoned, which is a continuation-in-part of application No. 08/870,370, Jun. 6, 1997, which is a continuation-in-part of application No. 08/886,280, Jul. 1, 1997, Pat. No. 5,846,729.

[51] Int. Cl.$^7$ .................................................. C12Q 1/68

[52] U.S. Cl. .................................... 435/6; 436/501

[58] Field of Search ......................... 435/6, 501; 935/77, 935/78

[56] References Cited

U.S. PATENT DOCUMENTS

| | | | |
|---|---|---|---|
| 4,220,450 | 9/1980 | Maggio | 23/230 B |
| 4,469,863 | 9/1984 | Ts'o et al. | 536/27 |
| 4,787,963 | 11/1988 | MacConnell | 204/180.1 |

(List continued on next page.)

FOREIGN PATENT DOCUMENTS

| | | |
|---|---|---|
| 0 232 967 | 8/1987 | European Pat. Off. . |
| 92 18650 | 10/1992 | WIPO . |
| 93 24652 | 12/1993 | WIPO . |
| 94 25477 | 11/1994 | WIPO . |
| 97 12995 | 4/1997 | WIPO . |

OTHER PUBLICATIONS

Perry–O'Keefe et al., "Peptide Nucleic Acid Pre–Gel Hybridization: An Alternative to Southern Hybridization," 93 Proc. Natl. Acad. Sci. USA 14670 (Dec. 1996).

Smulevitch et al., "Enhancement of Strand Invasion by Oligonucleotides Through Manipulation of Backbone Charge," 14 Nature Biotechnology 1700 (Dec. 1996) (disclosed in Landsdorp, "Close Encounters of the PNA Kind," 14 Nature Biotechnology 1653 (Dec. 1996)).

Lansdorp, "Close Encounters of the PNA Kind," 14 Nature Biotechnology 1653 (Dec. 1996).

Egholm et al., "PNA Hybridizes to Complementary Oligonucleotides Obeying the Watson–Crick Hydrogen–Bonding Rules," 365 Nature 566 (1993).

Tomac et al., "Ionic Effects on the Stability and Conformation of Peptide Nucleic Acid Complexes," 118 J.Am.Chem.Soc. 5544 (1996).

(List continued on next page.)

*Primary Examiner*—Ardin H. Marschel
*Attorney, Agent, or Firm*—Caesar, Rivise, Bernstein, Cohen & Pokotilow, Ltd.

[57] ABSTRACT

The invention provides a method for rapidly, economically and efficiently sequencing and assaying nucleotides in a fluid medium using laser induced fluorescence of antisense probes. The probes can have anionic backbones of reduced negative charge. Suitable probes can include methylphosphonate backbones. When the hybridization complexes and unhybridized probes are separated prior to detection, the fluorescent intensity of the fluid test medium is inversely proportional to the number of mismatches between the probe and target. When the hybridization complexes and unhybridized probes are not separated prior to detection, the fluorescent intensity of the fluid test medium is inversely proportional to the hybridization efficiency of the probes with respect to the target sequence and proportional to the number of mismatches between the probe and target. The method can be used to identify accessible regions in folded nucleotide sequences, to determine the number of mismatched pairs in a hybridization complex, and to map genomes.

31 Claims, 5 Drawing Sheets

U.S. PATENT DOCUMENTS

| | | | |
|---|---|---|---|
| 4,963,477 | 10/1990 | Tehen | 435/6 |
| 5,100,775 | 3/1992 | Smyczek et al. | 435/6 |
| 5,142,047 | 8/1992 | Summerton et al. | 544/118 |
| 5,166,315 | 11/1992 | Summerton et al. | 528/406 |
| 5,166,330 | 11/1992 | Engles et al. | 536/27 |
| 5,217,592 | 6/1993 | Jones | 204/299 R |
| 5,217,866 | 6/1993 | Summerton et al. | 435/6 |
| 5,223,618 | 6/1993 | Cook et al. | 544/276 |
| 5,310,650 | 5/1994 | McMahon et al. | 435/6 |
| 5,332,659 | 7/1994 | Kidwell | 435/6 |
| 5,405,938 | 4/1995 | Summerton et al. | 528/406 |
| 5,470,974 | 11/1995 | Summerton et al. | 544/118 |
| 5,501,949 | 3/1996 | Marshall | 435/5 |
| 5,503,980 | 4/1996 | Cantor | 435/6 |
| 5,521,063 | 5/1996 | Summerton et al. | 435/6 |
| 5,538,848 | 7/1996 | Livak et al. | 435/5 |
| 5,539,082 | 7/1996 | Nielsen et al. | 530/300 |
| 5,541,307 | 7/1996 | Cook et al. | 536/23.1 |
| 5,587,469 | 12/1996 | Cook et al. | 536/23.1 |
| 5,594,138 | 1/1997 | Dykstra et al. | 540/596 |
| 5,602,240 | 2/1997 | De Mesmaeker et al. | 536/22.1 |
| 5,610,289 | 3/1997 | Cook et al. | 536/25.34 |
| 5,618,704 | 4/1997 | Sanghvi et al. | 435/91.5 |
| 5,623,065 | 4/1997 | Cook et al. | 536/23.1 |
| 5,632,957 | 5/1997 | Heller et al. | 422/68.1 |
| 5,674,698 | 10/1997 | Zarling et al. | 435/792 |
| 5,677,437 | 10/1997 | Teng et al. | 536/23.1 |
| 5,747,247 | 5/1998 | Kowalczykowski et al. | 435/6 |
| 5,846,729 | 12/1998 | Wu et al. | 435/6 |

OTHER PUBLICATIONS

Coghlan, "One–Step DNA test in a tube," New Scientist, p. 21 (Nov. 5, 1994).

"PNA Oligomers as Hybridization Probes," vol. 1, Issue 2 of PerSeptive Biosystems Magazine, 1995.

Heppell–Parton, "Gene Mapping by Fluorescence in Situ Hybridization," p. 350–54, in *Molecular Biology and Biotechnology: A Comprehensive Desk Reference* (Myers, ed. 1995).

Matthews et al., "Analytical Strategies for the Use of DNA Probes," 169 Analystical Biochemistry 1 (1988).

Carlsson C. et al., "Screening for Genetic Mutations," Nature, 380:207, Mar., 1996.

Jensen et al., "Kinetics for Hybridization of Peptide Nucleic Acids (PNA) with DNA and RNA Studied with the BIAcore Technique," 36(16) Biochem. 5072 (Apr. 1997).

Grunstein et al., "Colony Hybridization: A Method for the Isolation of Cloned DNAs that Contain a Specific Gene," Proc. Nat'l Acad. Sci., 72(10):3961–3965, 1975.

Meinkoth et al., "Hybridization of Nucleic Acids Immobilized on Solid Supports," Analytical Biochemistry, 138:267, 1984.

Thomas, "Hybridization of Denatured RNA and Small DNA Fragments Transferred to Nitrocellulose," Proc. Nat'l Acad. Sci., 77(9):5201–5205, 1980.

Wetmur, Biopolymers, 14:2517–2524, 1975.

Chang et al., Biopolymers, 13:1847–1858, 1974.

Zhang et al., "Single–base mutational analysis of cancer and genetic diseases using membrane bound modified oligonucleotides," 19(14) Nucleic Acids Research 3929–3933 (Jul. 25, 1991).

R. Hogrefe et al., Nucleic Acids Research, 1993, vol. 21:2031–2039.

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
        (A) LENGTH: 40 bases
        (B) TYPE: nucleotide
        (C) STRANDEDNESS: double-stranded
        (D) TOPOLOGY: linear (xi) SEQUENCE DESCRIPTION: SEQ ID NO:1:

CTTCGAGATG TTCCGAGAGC TGAATGAGGC CTTGGAACTC                                    40

(2) INFORMATION FOR SEQ ID NO:2:

(i) SEQUENCE CHARACTERISTICS:
        (A) LENGTH: 40 bases
        (B) TYPE: nucleotide
        (C) STRANDEDNESS: double-stranded
        (D) TOPOLOGY: linear (xi) SEQUENCE DESCRIPTION: SEQ ID NO:2:

CTTCGAGATG TTCCGAGAGC AGAATGAGGC CTTGGAACTC                                    40

(2) INFORMATION FOR SEQ ID NO:3:

(i) SEQUENCE CHARACTERISTICS:
        (A) LENGTH: 40 bases
        (B) TYPE: nucleotide
        (C) STRANDEDNESS: double-stranded
        (D) TOPOLOGY: linear (xi) SEQUENCE DESCRIPTION: SEQ ID NO:3:

CTTCGAGATG TTCCGAGAGG AGAATGAGGC CTTGGAACTC                                    40

(2) INFORMATION FOR SEQ ID NO:4:

(i) SEQUENCE CHARACTERISTICS:
        (A) LENGTH: 40 bases
        (B) TYPE: nucleotide
        (C) STRANDEDNESS: double-stranded
        (D) TOPOLOGY: linear (xi) SEQUENCE DESCRIPTION: SEQ ID NO:4:

CTTCGAGATG TTCCGAGAGT ACAATGAGGC CTTGGAACTC                                    40

(2) INFORMATION FOR SEQ ID NO:5:

(i) SEQUENCE CHARACTERISTICS:
        (A) LENGTH: 40 bases
        (B) TYPE: nucleotide
        (C) STRANDEDNESS: double-stranded
        (D) TOPOLOGY: linear (xi) SEQUENCE DESCRIPTION: SEQ ID NO:5:

AACACCAGCT CCTCTCCCCA GCCAAAGAAG AAACCACTGG                                    40

(2) INFORMATION FOR SEQ ID NO:6:

(i) SEQUENCE CHARACTERISTICS:
        (A) LENGTH: 150 bases
        (B) TYPE: nucleotide
        (C) STRANDEDNESS: double-stranded (D) TOPOLOGY: linear (ii) MOLECULE TYPE: genomic DNA (xi) SEQUENCE DESCRIPTION: SEQ ID NO:6:

AACACCAGCT CCTCTCCCCA GCCAAAGAAG AAACCACTGG ATGGAGAATA TTTCACCCTT      60

CAGATCCGTG GGCGTGAGCG CTTCGAGATG TTCCGAGAGC TGAATGAGGC CTTGGAACTC     120

AAGGATGCCC AGGCTGGGAA GGAGCCAGGG                                      150

(2) INFORMATION FOR SEQ ID NO:7:

(i) SEQUENCE CHARACTERISTICS:
        (A) LENGTH: 150 bases
        (B) TYPE: nucleotide
        (C) STRANDEDNESS: double-stranded
        (D) TOPOLOGY: linear (xi) SEQUENCE DESCRIPTION: SEQ ID NO:7:

AACACCAGCT CCTCTCCCCA GCCAAAGAAG AAACCACTGG ATGGAGAATA TTTCACCCTT      60

CAGATCCGTG GGCGTGAGCG CTTCGAGATG TTCCGAGAGC AGAATGAGGC CTTGGAACTC     120

AAGGATGCCC AGGCTGGGAA GGAGCCAGGG                                      150

(2) INFORMATION FOR SEQ ID NO:8:

(i) SEQUENCE CHARACTERISTICS:
        (A) LENGTH: 150 bases
        (B) TYPE: nucleotide
        (C) STRANDEDNESS: double-stranded
        (D) TOPOLOGY: linear (xi) SEQUENCE DESCRIPTION: SEQ ID NO:8:

AACACCAGCT CCTCTCCCCA GCCAAAGAAG AAACCACTGG ATGGAGAATA TTTCACCCTT      60

CAGATCCGTG GGCGTGAGCG CTTCGAGATG TTCCGAGAGA AGAATGAGGC CTTGGAACTC     120

AAGGATGCCC AGGCTGGGAA GGAGCCAGGG                                      150

(2) INFORMATION FOR SEQ ID NO:9:

(i) SEQUENCE CHARACTERISTICS:
        (A) LENGTH: 120 bases
        (B) TYPE: nucleotide
        (C) STRANDEDNESS: double-stranded
        (D) TOPOLOGY: linear (xi) SEQUENCE DESCRIPTION: SEQ ID NO:9:

GCCAACTGGC CAAGACCTGC CCTGTGCAGC TGTGGGTTGA TTCCACACCC CCGCCCGGCA      60

CCCGCGTCCG CGCCATGGCC ATCTACAAGC AGTCACAGCA CATGACGGAG GTTGTGAGGC     120

(2) INFORMATION FOR SEQ ID NO:10:

(i) SEQUENCE CHARACTERISTICS:
        (A) LENGTH: 18 bases
        (B) TYPE: nucleotide with four methylphosphonate
            substitutions along its backbone
        (C) STRANDEDNESS: single-stranded
        (D) TOPOLOGY: linear (xi) SEQUENCE DESCRIPTION: SEQ ID NO:10:

CCTCATTCAG CTCTCGGA                                                    18

(2) INFORMATION FOR SEQ ID NO:11:

(i) SEQUENCE CHARACTERISTICS:

```
        (A) LENGTH: 18 bases
        (B) TYPE: nucleotide with nine methylphosphonate
            substitutions along its backbone
        (C) STRANDEDNESS: single-stranded
        (D) TOPOLOGY: linear (xi) SEQUENCE DESCRIPTION: SEQ ID NO:11:

CCTCATTCAG CTCTCGGA                                                18

(2) INFORMATION FOR SEQ ID NO:12:

(i) SEQUENCE CHARACTERISTICS:
        (A) LENGTH: 18 bases
        (B) TYPE: nucleotide with 18 methylphosphonate
            substitutions along its backbone
        (C) STRANDEDNESS: single-stranded
        (D) TOPOLOGY: linear (xi) SEQUENCE DESCRIPTION: SEQ ID NO:12:

CCTCATTCAG CTCTCGGA                                                18
```

SOLUTION HYBRIDIZATION OF NUCLEIC ACIDS WITH ANTISENSE PROBES HAVING MODIFIED BACKBONES

CROSS-REFERENCE TO RELATED APPLICATION

This application is a continuation-in-part of our earlier patent applications, U.S. patent applications Ser. Nos. 08/807,901, now abandoned, 08/870,370, 08/886,280, now U.S. Pat. No. 5,846,729; respectively filed Feb. 27, 1997, Jun. 6, 1997, and Jul. 1, 1997.

BACKGROUND OF THE INVENTION

1. Field of Invention

The invention relates to methods of sequencing or assaying nucleotides in solution using antisense probes having their backbones modified to alter their binding characteristics. In particular, the invention relates to sequencing or assaying nucleotides in solution using partially anionic antisense probes, which are not as anionic as unmodified DNA/RNA (i.e., purely phosphodiester) probes, or using nonionic antisense probes.

2. Description of Related Art

DNA/RNA analogs having modified backbones have been employed in a variety of contexts, including therapeutics and diagnostics. In the therapeutic context, modifications of oligonucleotides have largely been motivated by a desire to enhance nuclease resistance and thus increase the longevity of oligonucleotides in vivo. These modifications have generally taken place on the phosphorus atom of the sugar-phosphate backbone, converting the native phosphodiester backbone to other forms. Phosphorothioates, methyl phosphonates, phosphoramidates and phosphotriesters have been reported to confer various levels of nuclease resistance; however, it has been reported that the phosphate modified oligonucleotides have generally suffered from inferior hybridization properties. See, e.g., Cohen, J. S., ed. Oligonucleotides: Antisense Inhibitors of Gene Expression, (CRC Press, Inc., Boca Raton Fla., 1989) and U.S. Pat. No. 5,610,289 to Cook et al.

Despite such reports of inferior hybridization properties, it has been theorized that hybridization efficiency could be improved by eliminating the negative charge on oligonucleotide probes (or going a step further to provide positively charged probes), to thereby eliminate the unfavorable electronic interaction between the probe and the negatively charged target. Thus, much of the DNA/RNA analog art has focused on hybridization employing non-ionic and cationic analogs. See, e.g., U.S. Pat. Nos. 5,677,437 to Teng et al., 5,623,065 to Cook et al., 5,618,704 to Sanghvi et al., 5,602,240 to De Mesmaeker et al., 5,587,469 to Cook et al., 5,541,307 to Cook et al., 5,521,063 to Summerton et al., 5,470,974 to Summerton et al., 5,405,938 to Summerton et al., 5,223,618 to Cook et al., 5,166,330 to Engels et al., 5,166,315 to Summerton et al., 5,142,047 to Summerton et al. and 4,469,863 to Ts'o et al.

A peptide nucleic acid (PNA) is an example of a non-ionic DNA/RNA analog. See, e.g., U.S. Pat. No. 5,539,082 to Nielsen et al. Antisense probes comprising PNA sequences have been employed to detect target nucleotide sequences. For example, U.S. Pat. No. 5,503,980 to Cantor suggests employing PNA probes in a method of sequencing a nucleic acid by hybridizing the nucleic acid with a set of PNA probes containing random, but determinable, base sequences within the single stranded portion adjacent to a double stranded portion, wherein the single stranded portion of the set preferably comprises every possible combination of sequences over a predetermined range. Hybridization occurs by complementary recognition of the single stranded portion of a target with the single stranded portion of the probe and is thermodynamically favored by the presence of adjacent double strandedness of the probe.

However, although Cantor discloses that the nucleic acids can be PNAs, it does not disclose or suggest utilizing such probes in the absence of a solid support. Moreover, the present invention does not require the adjacent construct of DNA material being tested.

In addition to teaching the use of a solid support like Cantor, Perry-O'Keefe et al., "Peptide Nucleic Acid Pre-Gel Hybridization: An Alternative to Southern Hybridization," 93 Proc. Natl. Acad. Sci. USA 14670 (December 1996) also teaches that PNA does not generally bind well to double stranded DNA (dsDNA). See Perry-O'Keefe et al. at page 14673, footnote. Moreover, the homopyrimidine PNA constructs which have been found to bind dsDNA well would not be useful as probes. Applicants have discovered that the qualification which suggests that only homopyrimidine can bind with dsDNA by strand invasion is incorrect and arises from the hybridization conditions employed. Smulevitch et al., "Enhancement of Strand Invasion by Oligonucleotides Through Manipulation of Backbone Charge," 14 Nature Biotechnology 1700 (December 1996) (disclosed in Landsdorp, "Close Encounters of the PNA Kind," 14 Nature Biotechnology 1653 (December 1996)) discloses using PNA primers to hybridize with dsDNA. However, Smulevitch et al. teaches the use of gels in detecting hybridization, and does not suggest the use of fluorescent markers.

Many types of sample analysis rely upon the fluorescent properties of a marker. Fluorescence occurs when a molecule excited by light of one wavelength returns to the unexcited (ground) state by emitting light of a longer wavelength. The exciting and emitted light, being of different wavelengths, can be separated from one another using optical filters, a camera or a CCD. Fluorescence has been used to visualize certain molecules (and hence structures) by light microscopy for many years, and is also used in other analytical techniques, such as flow cytometry. Further, the emission of fluorescence showing different colors can be detected by a human eye, a camera, a charge coupled device (CCD) or a photomultiplier.

For example, U.S. Pat. No. 5,594,138 to Dykstra et al. discloses a method of fluorescent detection of a nucleic acid. The method comprises contacting the nucleic acid with a fluorescent marker that is a bis-dicationic aryl furan compound and exposing the nucleic acid to light at a frequency inducing fluorescence of the fluorescent marker. The fluorescent marker may be conjugated to a nucleotide sequence as a probe for hybridization studies, or it may be conjugated to numerous reagents for in situ labeling studies. Hybridization occurs on a solid support.

U.S. Pat. No. 4,963,477 to Tchen discloses a probe of high sensitivity containing a modified nucleic acid, which can be recognized by specific antibodies.

Fluorescent In Situ Hybridization (FISH) is a technique comprising detecting fluorescent probe binding to human chromosomes by attaching DNA to a solid support, such as a glass slide. See, e.g., K. H. Andy Choo, Ed., "In Situ Hybridization Protocols," Chapters 2 and 4 (Humana Press, Totowa, N.J., 1994). Like all other conventional detection methods comprising hybridization with probes, this method relies on the solid support to keep the two complementary strands of DNA apart while the probe hybridizes with one of the strands. In addition, FISH requires a complicated buffer and temperature control protocol, with overnight incubation.

U.S. Pat. Nos. 5,538,848 to Livak et al. and 4,220,450 to Maggio disclose fluorescence-based detection of nucleotide sequences using oligonucleotide probes in solution; however, these patents require the use of a quenching agent in combination with a reporting agent, so as to distinguish between the signals generated by hybridized probes and unhybridized probes. Livak et al. also requires the use of enzymes in its disclosed method. Quenching agents and enzymes add complexity and expense to the methods.

U.S. Pat. No. 5,332,659 to Kidwell discloses a method for detecting nucleotide sequences in solution using probes comprising at least two fluorophore moieties. The fluorophores must be selected to electronically interact with each other when close enough to vary the wavelength dependence of their spectra. Unhybridized probes are much more flexible than probes hybridized to the target sequence, and consequently the two fluorophore moieties on each probe are more likely to be close to each other when the probe is unhybridized than when the probe is hybridized. Thus, a change in emission wavelength correlated with free probe can be monitored as an indication of the amount of free probe in the sample.

U.S. Pat. No. 5,674,698 to Zarling et al. discloses fluorescent assaying methods comprising the use of "up-converting" labels, which fluoresce at frequencies higher than their excitation frequencies and at wavelengths lower than their excitation wavelengths. Zarling et al. strongly teaches away from assays using down-converting labels (i.e., labels that fluoresce at frequencies lower than their excitation frequencies and at wavelengths higher than their excitation wavelengths) due to poor signal-to-noise ratios.

Until the present invention, however, it has not been possible to rapidly test for the presence of nucleotide sequences in solution using a method which does not destroy the sample, is less hazardous to laboratory personnel than radiation based assays, does not require the cost and delay of separating unhybridized probes from hybridization complexes, does not require the provision of quenching agents, does not require the provision of enzymes, does not require the provision of multiple interactive reporting moieties on, or in the vicinity of, each probe, does not require the provision of up-converting labels, and is readily automated. Time and cost efficient detection of mutant genetic sequences has been the rate limiting step in correlating mutant genotypes with altered phenotypes. Although conventional DNA sequencing methods have been considered to be the most accurate means of identifying mutations, these methods have been relatively slow and labor intensive, and are not particularly well-suited to rapidly screening large numbers of samples of genomic DNA for purposes including medical diagnosis, genomic sequencing and mapping.

All references and prior patent applications cited herein are incorporated herein by reference in their entireties.

SUMMARY OF THE INVENTION

The present invention provides a method for detecting at least one single stranded or double stranded nucleobase-containing target sequence in a fluid medium, said method comprising:

adding to said fluid medium antisense probes capable of forming hybridization complexes with said at least one target sequence, wherein said antisense probes comprise a backbone having a charge that is less negative than a comparable phosphodiester backbone;

separating unhybridized antisense probes from said hybridization complexes to form a test medium;

irradiating said test medium with a laser beam having a wavelength which excites fluorescent markers in said hybridization complexes and causes said fluorescent markers to emit fluorescent light;

measuring an intensity of said emitted fluorescent light; and comparing said measured intensity with a reference intensity to detect whether said fluid medium contains said at least one target sequence, wherein said measured intensity is inversely proportional to a number of base mismatches between said at least one target sequence and said antisense probes, over a range inclusive of 0 base mismatches through at least 3 base mismatches, and wherein said method other than said separating step is entirely conducted without binding said antisense probe, said at least one target sequence or said hybridization complexes to a solid support or gel.

Also provided is a method for detecting at least one single stranded or double stranded nucleobase-containing target sequence in a fluid medium, said method comprising:

adding to said fluid medium antisense probes capable of forming hybridization complexes with said at least one target sequence, wherein said antisense probes comprise a backbone having a charge that is less negative than a comparable phosphodiester backbone;

irradiating said fluid medium with a laser beam having a wavelength which excites fluorescent markers in said hybridization complexes and causes said fluorescent markers to emit fluorescent light;

measuring an intensity of said emitted fluorescent light; and comparing said measured intensity with a reference intensity to detect whether said fluid medium contains said at least one target sequence, wherein said measured intensity is proportional to a number of base mismatches between said at least one target sequence and said antisense probes, over a range inclusive of 0 base mismatches through at least 3 base mismatches, and wherein said method is conducted without separating unhybridized probes from hybridization complexes prior to said signal detecting, and without providing a signal quenching agent on said antisense probes or on said at least one nucleobase-containing target sequence.

The invention thus provides methods for rapidly, economically and efficiently sequencing and assaying nucleobase-containing sequences in a fluid medium using laser induced fluorescence of antisense probes, which can be used to detect target nucleobase-containing sequences, to identify accessible regions in folded nucleobase-containing sequences, to determine the number of mismatched pairs in a hybridization complex, and to map genomes by screening a genomic library with a plurality of probes.

The methods can be conducted without separating unhybridized probes from the hybridization complexes prior to signal detecting, without providing a signal quenching agent on, or in the vicinity of, the probe or the nucleobase-containing sequence, without the use of enzymes, and without the use of up-converting labels.

BRIEF DESCRIPTION OF THE DRAWINGS

The invention will be described in conjunction with the following drawings in which like reference numerals designate like elements and wherein.

DEFINITIONS

Figure 1:
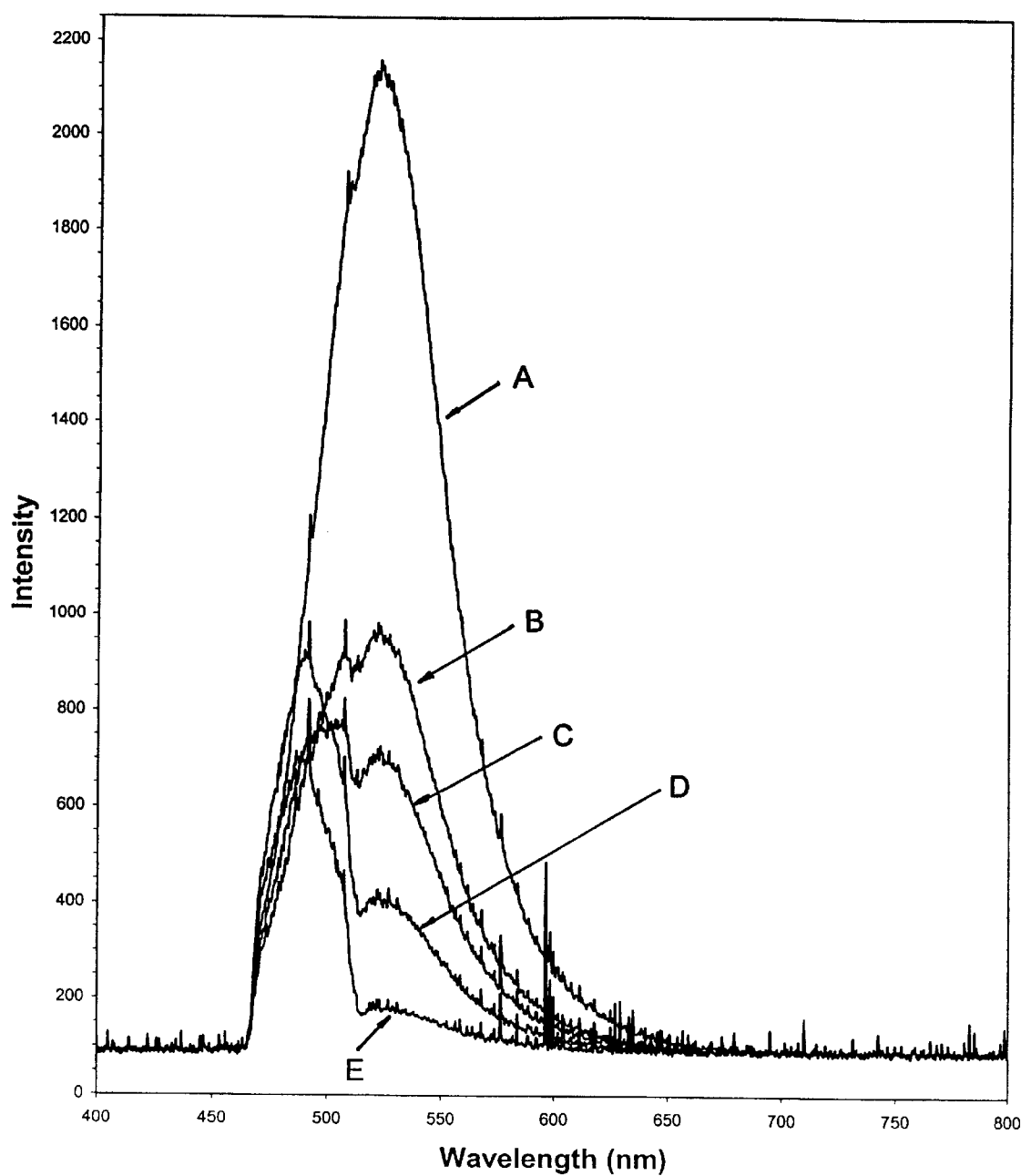
FIG. 1 shows the fluorescent spectra resulting from assaying for several different targets and a non-target with 25% methylated DNA probes.

Although the terminology employed herein generally conforms to conventional usage, the following definitions are provided to remove any doubt as to the meaning of selected terminology employed to help define the limits of the invention.

The expression "nucleobase-containing sequence" as used herein encompasses, e.g., DNA, RNA, modified nucleic acid sequences and PNA. The term is intended to encompass all molecules capable of specifically hybridizing via base pairing to complementary (or partially complementary) segments of DNA and/or RNA.

The expression "antisense probes" as used herein includes any nucleobase-containing sequence capable of specifically binding to another nucleobase-containing sequence having a base sequence complementary to the base sequence of the probe. The antisense probes of the invention can be complementary to either strand of dsDNA, for example.

An unmodified nucleotide sequence having a phosphodiester backbone is "comparable" to a nucleobase-containing sequence having a modified backbone if the two sequences have identical base sequencing. Thus, the backbones of such sequences are also comparable.

DETAILED DESCRIPTION OF PREFERRED EMBODIMENTS

The invention preferably utilizes anionic antisense probes of reduced negative charge to detect and/or characterize nucleobase-containing sequences in a sample.

An anionic probe of the invention has reduced negative charge due to the substitution of at least one, and preferably less than all negatively charged phosphate groups of the probe with a neutral group. Preferably, about half of the phosphate groups of the probe are substituted with neutral groups, more preferably about one-quarter of the phosphate groups of the probe are substituted with neutral groups.

It is preferred that the neutral group substituted for the native phosphate group be a methylphosphonate group; however other substituents are within the scope of the invention, including aminoethyl phosphonates, hydroxymethyl phosphonates, methylphosphonothioates, s-methyl phosphorothioates, phosphoramidites, and the like. Suitable methods for making such backbone substitutions are known in the art.

The probe can be homogeneously or heterogeneously substituted with neutral substituents. In homogeneous substitution schemes, only one type of backbone modification would be made to the probe. For example, in homogeneous substitution, the only modifications to the probe might be the substitution of methylphosphonate groups for phosphate groups, whereas in heterogeneous substitution, the probe could comprise a segment of PNA linked to a segment of methylphosphonated DNA.

Probe sequences having any length from 8 to 20 bases are preferred since this is the range within which the smallest unique DNA/RNA sequences of prokaryotes and eukaryotes are found. Probes of at least 18 bases are particularly preferred since this is the length of the smallest unique sequences in the human genome. However, a plurality of shorter probes can be used to detect a nucleobase-containing sequence having a plurality of non-unique target sequences therein, which combine to uniquely identify the nucleobase-containing sequence.

At least the probes of the invention comprising PNA are able to form triplex complexes with dsDNA and duplex complexes with RNA or ssDNA. Such probes are also able to form triplex complexes wherein a first probe binds with RNA or ssDNA and a second ssDNA strand binds with the resulting duplex complex. See, e.g., Egholm et al., "PNA Hybridizes to Complementary Oligonucleotides Obeying the Watson-Crick Hydrogen-Bonding Rules," 365 Nature 566 (1993), and Tomac et al., "Ionic Effects on the Stability and Conformation of Peptide Nucleic Acid Complexes," 118 J.Am.Chem.Soc. 5544 (1996).

In the probes according to the invention, the bases attached to the backbone are primarily naturally occurring nucleobases attached at the position required by probe manufacture. Alternatively, the bases may be non-naturally occurring nucleobases (nucleobase analogs), other base-binding moieties, aromatic moieties, (C1–C4) alkanoyls, hydroxyls or even hydrogens. It will be understood that the term nucleobase includes nucleobases bearing removable protecting groups. Furthermore, at least one base on the backbone can be replaced with, or substituted with, a DEA intercalator, a reporter ligand such as, for example, a fluorophore, radio label, spin label, hapten, or a protein-recognizing ligand such as biotin. Preferred detectable labels include a radioisotope, a stable isotope, an enzyme, a fluorescent chemical, a luminescent chemical, a chromatic chemical, a metal, an electric charge, or a spatial structure.

In particularly preferred embodiments, the probe comprises an antisense sequence covalently bonded to a fluorescent marker, which fluoresces when irradiated with a laser. Preferred fluorescent markers include biotin, rhodamine and fluorescein.

In embodiments of the invention wherein unhybridized probe is separated from probe/target hybridization complexes, the fluorescent intensity of the hybridization solution is inversely proportional to the number of mismatches between the probe and target, preferably over a range inclusive of 0 base mismatches through at least 3 base mismatches.

In embodiments of the invention wherein unhybridized probe is not separated from hybridization complexes prior to measuring fluorescence, the fluorescent intensity is proportional to the amount of free probe in solution and to the number of mismatches between the probe and target, and inversely proportional to the amount of hybridized probe in solution. That is, there is a quenching effect associated with hybridization of the probe and target sequence. The quenching effect varies with the marker selected. This effect enables the method of the invention to detect hybridization without employing a quenching agent on the probe (to quench unhybridized probe signal) or on the target sequence (to quench hybridized probe signal), as required by, e.g., Livak et al. and Maggio, supra.

Unlike Kidwell, supra, the instant invention does not require a plurality of electronically interacting fluorophores on each probe, because the fluorescent intensity quenching effect detected by the instant invention is not the same as the emission wavelength shift detected in Kidwell, which is caused by intramolecular excimer formation between adjacent fluorophores. The quenching effect of the instant invention is apparent with only one fluorophore per probe (although a plurality of fluorophores per probe are contemplated for certain embodiments).

In certain embodiments, the fluorescent marker is provided at the 5' terminal of the probe with a short linker to minimize interaction with the probe. However, the position of the marker within the probe does not appear to be particularly significant.

In order to distinguish a mutant nucleotide sequence from a reference nucleotide sequence, wherein the two sequences differ by as little as a single base, it is preferred to design the probe so that the mutant portion of the mutant nucleotide corresponds to the center of the probe. This design results in a higher hybridization yield and a more stable hybrid than when the mutant portion of the nucleotide corresponds to a terminus of the probe, since the bonding mismatch between probe and nucleotide is located centrally within the probe.

Probes are added to a fluid medium suspected of containing at least one nucleotide sequence, and/or a mutant version of the at least one sequence. The fluid medium can be any conventional medium known to be suitable for preserving nucleotides or other nucleobase-containing sequences. See, e.g., Sambrook et al., "Molecular Cloning: A Lab Manual," 2d (1989). For example, the fluid medium can be in the form of a liquid comprising nucleotides, water, buffers and surfactants.

The nucleotides in the fluid medium can be obtained from clinical samples by any conventional method, including an automated method. Examples of such methods are summarized in, e.g., Sambrook et al., Vol. 2, pp. 9.16–9.19 and 7.6 to 7.7. An example of an automated nucleic acid purifying apparatus is the BioRobot 9600 manufactured by Quiagen (Chatsworth, Calif., USA).

For example, a variety of diseases are known to be linked with the presence of mutant DNA in an individual's genome. If the sequences of the wild type DNA and the mutant DNA are known, it is possible to isolate these nucleotide sequences from clinical samples using conventional technology. PCR is the preferred method of amplifying nucleotides from clinical samples. PCR is conducted using a primer which is capable of amplifying the wild type DNA and the mutant DNA.

The nucleobase-containing sequences are added to the fluid medium in a known concentration, since the concentration can affect the magnitude of the signal (e.g., fluorescent intensity) generated in subsequent steps in the inventive method. The nucleobase-containing sequence concentration can be determined by, e.g., measuring the UV absorption at 260 nm.

The isolated nucleobase-containing sequences are added to the fluid medium and denatured prior to being detected. Preferably, the denaturation is conducted at about 90° C. to about 100° C. from about 30 seconds to about 5 hours in the presence of antisense probe.

Preferably, probes are added to the fluid medium in a concentration 0.05 to 100 times the concentration of the nucleobase-containing sequence to be detected.

Hybridization between complementary bases occurs under a wide variety of conditions having variations in temperature, salt concentration, electrostatic strength, and buffer composition. Examples of these conditions and methods for applying them are known in the art. See, e.g., Perry-O'Keefe et al., Egholm et al., Tomac et al., Sambrook et al., Vol. 2 pp. 9.47–9.55 and the Pre-Gel Hybridization Technique taught in Vol. 4, No. 3 of PerSeptive Biosystems Magazine.

It is preferred that hybridization complexes be formed at a temperature of about 4° C. to about 75° C. for about 2 minutes to about 24 hours. It is particularly preferred to conduct denaturing for no more than 60 minutes in the presence of the probes, after which the temperature is passively cooled to room temperature without quenching.

It is possible to facilitate hybridization in solution by using certain reagents. Preferred examples of these reagents include single stranded binding proteins such as Rec A protein, T4 gene 32 protein, E. coli single stranded binding protein, major or minor nucleic acid groove binding proteins, divalent ions, polyvalent ions, and intercalating substances such as ethidium bromide, actinomycin D, psoralen, and angelicin.

The preferred markers for use in the invention are fluorophores. As will be appreciated by the skilled artisan, the wavelength preferably selected to induce fluorescence of the fluorescent marker is known in the art as the "excitation maximum," i.e., that wavelength which is absorbed by a molecule and excites that molecule to a higher electronic state. When the marker molecule passes from the higher to a lower electronic state, the molecule emits a type of visible radiation, i.e., fluorescence, at a wavelength referred to as the "emission maximum." It is at least this fluorescence that is detected in the present invention. The detectable signal emitted by the compound can be detected using techniques known in the art, for example by observation with the human eye, using electronic means for detecting a generated wavelength (e.g., cameras and CCDs), and the like. Advantageously, the wavelength of fluorescence is sufficiently removed from that of the exciting light to allow good separation of the two wavelengths by optical filters. Contrary to the teachings of Zarling et al., supra, the present invention is sufficiently sensitive to obtain good fluorescence data with down-converting labels.

The excitation wavelength is selected (by routine experimentation and/or conventional knowledge) to correspond to this excitation maximum for the marker being used, and is preferably 200 to 1000 nm. For example, when the marker is fluorescein, the preferred wavelength of excitation is about 488 nm. Fluorescent dyes are preferably selected to have an emission wavelength of 200 to 1000 nm.

In preferred embodiments, an argon ion laser is used to irradiate the marker with light having a wavelength in a range of 400 to 520 nm, and fluorescent emission is detected in a range of 500 to 750 nm.

An apparatus for performing the inventive method can comprise a fluid medium container for containing the fluid medium; a laser for irradiating the nucleobase-containing sequence; a CCD fluorescence detector and/or photomultiplier for detecting fluorescence induced by the laser; a data analysis device for analyzing data generated by the fluorescence detector; and an output device which reports the data analysis generated by the data analysis device.

Unlike certain prior art methods, no separation of the hybridization complexes from the uncomplexed probes is necessary in certain embodiments of the present method. In certain prior art methods, unhybridized probes and hybridized probes must be separated to enhance the signal to noise ratio (i.e., the ratio of the hybridization complex signal to the unhybridized probe signal or noise), enabling detection of hybridization. In the present separation-free method, the change in the overall signal is monitored without performing the additional burdensome step of separating the hybridized and unhybridized probes. The inventors have discovered that nucleotide sequence information can be determined by monitoring a change in the overall signal intensity, which is a function of hybridization and hybridization efficiency.

In particular, the inventors have discovered a signal quenching effect related to probe-nucleotide hybridization, wherein the intensity of laser induced fluorescence of an unbound probe exceeds that of the same probe bound to a nucleotide sequence. Therefore, a solution lacking any target sequences for probes therein will fluoresce more intensely than an otherwise identical solution containing target sequences and thus probe-nucleotide hybridization complexes.

Moreover, the intensity of laser induced fluorescence of hybridized probes is inversely proportional to the hybridization efficiency of the probes for their target sequences, in the separation-free embodiment of the invention. Therefore, a solution containing imperfectly complementary target sequences for probes therein will fluoresce more intensely than an otherwise identical solution containing perfectly complementary target sequences. A solution containing target sequences mismatching n bases of the probes therein will fluoresce more intensely than an otherwise identical solution containing target sequences mismatching less than n bases of the probes therein. Thus, a three mismatch solution fluoresces more intensely than a two mismatch solution, which fluoresces more intensely than a one mismatch solution, which fluoresces more intensely than a zero mismatch (completely complementary) solution.

The invention can be used to obtain nucleotide sequence information in a variety of ways.

In embodiments, a predetermined amount of at least one probe can be added to a predetermined volume of solution containing a predetermined amount of at least one nucleobase-containing sequence to be detected. After subjecting the sample to hybridizing conditions, the sample's laser induced fluorescent intensity can be measured. Sequence information regarding the at least one nucleobase-containing sequence in the sample can be determined by comparing the intensity with the intensity of at least one known sample against which the apparatus and the method are calibrated. Thus, a mutant form of the target sequence has been detected if, for example, (a) a sample containing sample DNA and probes hybridizable to a sequence of wild type DNA, fluoresces significantly more intensely than (b) a standard sample containing a probe perfectly complementary to the same sequence of the wild type DNA.

Similarly, a mutant form of the target sequence is detected if the sample does not fluoresce significantly less intensely than a standard sample containing a mutant form of the target sequence.

A significant difference in intensity is defined for present purposes as a difference not attributable to mere experimental variation. In some quenching effect analyses, the intensity of a perfectly matched probe and target sequence has been at least about 40% lower than the intensity (at the same wavelength) of an imperfectly matched probe and the same sequence. This value will vary along with the hybridization efficiency of a given case. However, those of ordinary skill in the art will readily appreciate that the actual value for any case being analyzed can be obtained empirically without undue experimentation.

The sensitivity of the invention appears to be most pronounced for DNA/RNA analog probes having reduced charge anionic backbones, such as methylphosphonate oligonucleotides. Probes having uncharged (i.e., neutral or non-ionic) backbones, such as PNA and methylene methyl amino oligonucleotides, also appear to outperform native (i.e., phosphodiester) oligonucleotides as probes.

Another embodiment of the invention comprises dividing a sample into equal portions and treating each portion as a separate sample as discussed above, except that a different probe is added to each portion. The intensities of the portions are compared to determine, inter alia, which probe is most complementary, and thus which target sequence is in the original sample. This embodiment of the method is advantageous in that the system does not need to be calibrated against a known sample.

Although solid supports and gels are not required to practice this invention, such supports can be used in embodiments of the invention to separate hybridized probes from unhybridized probes prior to measuring fluorescence, or for other purposes. For example, two similar types of probes differing by one base can be fixed to opposing internal surfaces of a container in which a sample is added. After subjecting the sample to hybridization conditions and fluorescence inducing radiation, the intensities of the fluorescence emitted from the opposing surfaces of the container can be compared to determine whether the sample contains a nucleobase-containing sequence perfectly complementary to either or both types of probes fixed to the surface.

A plurality of probes can be employed simultaneously to achieve a variety of effects. Several probes targeted for different segments of a single target sequence can be employed to enhance the reliability of the detection method. Similarly, one probe can target one strand of dsDNA, while another probe can target the complementary strand of dsDNA.

A preferred method of detecting whether DNA is mutant type or the corresponding wild type comprises the simultaneous use of (a) a first type of probe targeted to a sequence that occurs in both the wild type and mutant type DNA but is otherwise unique, and (b) a second type of probe targeted to a sequence unique to the mutant type DNA, wherein the first and second types of probe have different markers that produce distinguishable signals. Thus, detection of the first probe signal indicates that the test was run properly (i.e., the first probe functions as a positive control) and detection of the second probe signal indicates that the mutant type DNA is present. For example, one probe can have a fluorescein marker exhibiting a fluorescent emission intensity peak at 525 nm while the other probe can have a rhodamine marker exhibiting a fluorescent emission intensity peak at 580 nm.

The speed, accuracy and efficiency with which the invention is able to yield sequence data, coupled with the ability of laser induced fluorescence of probes to localize sequence portions within a longer sequence, make the invention an alternative to the FISH method for mapping genomes (compare, e.g., Heppell-Parton, "Gene Mapping by Fluorescence in Situ Hybridization," p. 350–54, in *Molecular Biology and Biotechnology: A Comprehensive Desk Reference* (Myers, ed. 1995)).

The invention provides an efficient method for analyzing nucleotide conformation, which is particularly useful for designing antisense drugs. Antisense drugs typically target mRNA for hybridization with an antisense sequence, so as to prevent translation of the mRNA into undesirable proteins. Unfortunately, the in situ folding of mRNA prevents some sequence portions along its length from being accessible to antisense sequences. Until now, drug designers have located accessible sequences by a method in which a series of antisense nucleotides complementary to different portions of the target mRNA are combined with the mRMA, and the best binding antisense nucleotide, presumably corresponding to the most accessible portion of the mRNA, is identified through slow and laborious tissue culture experiments, which can take at least about 45 days. See, e.g., Rawls, "Optimistic About Antisense," 75(22) Chem. Eng. News 35, 39 (Jun. 2, 1997). The accessible portions of mRNA can be identified using the instant invention without tissue culture experiments, since laser induced fluorescent intensity is inversely proportional to hybridization efficiency. The sequence emitting the lowest intensity has the highest hybridization efficiency with the target mRNA, and is presumably complementary to a segment that is not obstructed by in situ folding of mRNA.

The probes can be marked antisense drugs and/or can be analogs thereof. For example, it might be advantageous to design phosphorothioate oligonucleotide antisense sequences by performing laser induced fluorescent studies with such sequences marked with a fluorophore or with PNA probes similarly marked.

Moreover, the invention enables the length and other features of the antisense drugs to be readily fine tuned to optimize hybridization efficiency.

In contrast to prior art nucleotide sequence detection methods, the present invention makes it possible to limit the total volume of the fluid medium (i.e., the sample to be analyzed) in certain embodiments to about 5 microliters. Typically, the total volume is about 5 microliters to about 2000 microliters.

When testing for dsDNA using at least the PNA containing probes of the invention, if a result is obtained for which there remains doubt, a further test may be immediately performed on the sample by adding the complementary PNA containing probe to test the complementary strand of DNA. Alternatively, the test can be done with both the probe and complementary probe hybridized to each of the denatured DNA strands in the first instance and at the same time.

For forensic applications, samples can be tested, stored and then retested, at least with PNA containing probes, because PNA is expelled from hybridization over a couple of days, and DNA recombines over time and does not degrade by this procedure. Accordingly, a sample frozen after testing can be subsequently retested in the same tube a number of times.

Clinical samples can be tested using at least 2000 times less chemicals or genomic material (5 microliters vs. 10 milliliters) than is typical in conventional methods. Therefore, even using 10 or 20 times the concentration of probe conventionally used, the tests still only consume ⅕th to ⅒th the amount of probe, while obtaining a very decisive result.

The invention will be illustrated in more detail with reference to the following Examples, but it should be understood that the present invention is not deemed to be limited thereto.

EXAMPLES

DNA synthesis

The following 40 bp target DNA oligonucleotides were synthesized with a DNA synthesizer (Expedite 8909, PerSeptive Biosystems) using conventional reagents and protocols specified by the manufacturers of the reagents and synthesizer:

a) Target DNA A1 (wild type-strand A of SEQ ID NO:1) 5' CTT CGA GAT GTT CCG AGA GCT GAA TGA GGC CTT GGA ACT C 3' b) Target DNA B1 (wild type-strand B of SEQ ID NO:1) 5' GAG TTC CAA GGC CTC ATT CAG CTC TCG GAA CAT CTC GAA G 3' c) Target DNA A2 (1 base mismatch-strand A of SEQ ID NO:2) 5' CTT CGA GAT GTT CCG AGA GCA GAA TGA GGC CTT GGA ACT C 3' d) Target DNA B2 (1 base mismatch-strand B of SEQ ID NO:2) 5' GAG TTC CAA GGC CTC ATT CTG CTC TCG GAA CAT CTC GAA G 3' e) Target DNA A3 (2 base mismatch-strand A of SEQ ID NO: 3) 5' CTT CGA GAT GTT CCG AGA GGA GAA TGA GGC CTT GGA ACT C 3' f) Target DNA B3 (2 base mismatch-strand B of SEQ ID NO:3) 5' GAG TTC CAA GGC CTC ATT CTC CTC TCG GAA CAT CTC GAA G 3' g) Target DNA A3 (3 base mismatch-strand A of SEQ ID NO: 4) 5' CTT CGA GAT GTT CCG AGA GTA CAA TGA GGC CTT GGA ACT C 3' h) Target DNA B3 (3 base mismatch-strand B of SEQ ID NO:4) 5' GAG TTC CAA GGC CTC ATT GTA CTC TCG GAA CAT CTC GAA G 3' i) Untargeted DNA (strand A of SEQ ID NO:5) 5' AAC ACC AGC TCC TCT CCC CAG CCA AAG AAG AAA CCA CTG G 3' j) Untargeted DNA (strand B of SEQ ID NO:5) 5' CCA GTG GTT TCT TCT TTG GCT GGG GAG AGG AGC TGG TGT T 3'

The following dsDNAs were produced by a GeneAmp 2400 PCR system (Perkin Elmer):

a) a 150 bp DNA sequence from p53 wild type DNA AACACCAGCT CCTCTCCCCA GCCAAAGAAG AAACCACTGG ATGGAGAATA TTTCACCCTT CAGATCCGTG GGCGTGAGCG CTTCGAGATG TTCCGAGAGC TGAATGAGGC CTTGGAACTC AAGGATGCCC AGGCTGGGAA GGAGCCAGGG (SEQ ID NO:6)

b) a 150 bp DNA sequence from p53 mutated DNA with one base pair substitution (Q) AACACCAGCT CCTCTCCCCA GCCAAAGAAG AAACCACTGG ATGGAGAATA TTTCACCCTT CAGATCCGTG GGCGTGAGCG CTTCGAGATG TTCCGAGAGC AGAATGAGGC CTTGGAACTC AAGGATGCCC AGGCTGGGAA GGAGCCAGGG (SEQ ID NO:7)

c) a 150 bp DNA sequence from p53 mutated DNA with two base pair substitution (K) AACACCAGCT CCTCTCCCCA GCCAAAGAAG AAACCACTGG ATGGAGAATA TTTCACCCTT CAGATCCGTG GGCGTGAGCG CTTCGAGATG TTCCGAGAGA AGAATGAGGC CTTGGAACTC AAGGATGCCC AGGCTGGGAA GGAGCCAGGG (SEQ ID NO:8)

d) a 120 bp untargeted DNA used as a negative control GCCAACTGGC CAAGACCTGC CCTGTGCAGC TGTGGGTTGA TTCCACACCC CCGCCCGGCA
CCCGCGTCCG CGCCATGGCC ATCTACAAGC
AGTCACAGCA CATGACGGAG GTTGTGAGGC
(SEQ ID NO:9)

Synthesis of methylphosphonate oligonucleotides

Methylphosphonate oligonucleotides were synthesized according to the conventional protocols specified by the manufacture of the DNA synthesizer employed for the synthesis (Expedite 8909). The coupling time for methyl phosphonamidites was six minutes. Methyl phosphonamidites (bz-dA-Me, ibu-dC-Me, ibu-dG-Me and dT-Me phosphonamidite) and fluorescent phosphoramidite were purchased from Glen Research (Sterling, Va.). Phosphoramidites and reagents for synthesis were purchased from PerSeptive Biosystems. Ethylenediamine (EDA), acetonitrile (ACN), ammonium hydroxide and ethyl alcohol (EtOH) were purchased from Sigma-Aldrich.

The deprotection procedures were based on the one-pot procedure disclosed by R. Hogrefe et al., Nucleic Acids Research, 1993, Vol. 21:2031–2039.

Partially methylphosphonated oligonucleotides were deprotected and cleaved by adding 1 ml of a mixture of EtOH/ACN/water/ammonium hydroxide (40/40/10/10 (V/V %)) to a CPG column along with the synthesized nucleotides, and driving the mixture back and forth through the column five times using a syringe. After thirty minutes at room temperature, 1 ml of EDA was added to the column, driven back and forth through the column five times, and then held at room temperature for six hours. The resulting solution was then collected from the column. The column was then washed twice using 1 ml of a 1:1 mixture of ACN and water, and the eluate was collected and added to the solution collected from the column prior to washing the column. This combined solution was then neutralized to pH 7 in an ice bath using 6 N HCl.

Completely methylphosphonated oligonucleotides were deprotected and cleaved by adding 1 ml of a mixture of EtOH/ACN/ammonium hydroxide (45/45/10 (V/V %)) to a CPG column along with the synthesized nucleotides, and driving the mixture back and forth through the column five times using a syringe. After thirty minutes at room temperature, 1 ml of EDA was added to the column, driven back and forth through the column five times, and then held at room temperature for six hours. The resulting solution was then collected from the column. The column was then washed twice using 1 ml of a 1:1 mixture of ACN and water, and the eluate was collected and added to the solution collected from the column prior to washing the column. This combined solution was then neutralized to pH 7 in an ice bath using 6 N HCl containing 10% acetonitrile (V/V %).

After deprotection, the oligonucleotides were purified by reverse-phase HPLC, using a 7.8×300 mm Delta Pak C18 column (Waters, Milford, Mass.). The solvents were 0.1 M triethylammonium acetate (TEAA), pH 7, and a mixture of ACN and water (95:5 (V:V)). The gradient was from 10 to 40% (Vol. % TEAA in ACN/Water) over 30 minutes. The flow rate was 4 ml/minute.

Collected fractions having the desired purity were pooled and lyophilized with ACN/water (1:1) three times to remove TEAA. The resulting dried pellets were soluble in water (if partially methylphosphonated) or in a 20/80% mixture of ACN/water (if completely methylphosphonated.

The following methylphosphonate oligonucleotide probes were synthesized and purified:

1) Probe 1 was an anionic 18 mer modified backbone DNA probe with 4 methylated groups:

5' Fluo-C CTmC ATTm CAG CmTC TCmG GA 3' (SEQ ID NO:10)

2) Probe 2 was an anionic 18 mer DNA probe which was one-half methylated:

5' Fluo-Cm CTmC AmTTm CAmG CmTCm TCmG GmA 3' (SEQ ID NO:11)

3) Probe 3 was a non-ionic 15 mer DNA probe which was fully methylated:

5' CmTmCm AmTmTm CmAmGm CmTmCm TmCmGm-Fluo 3' (SEQ ID NO:12)

Hybridization

Examples 1A–1E

In each of Examples 1A–1E, 40 pmol of 40 mer synthesized dsDNA was added to 100 pmol of methylphosphonate oligonucleotide probe 1 (SEQ ID NO:10) and mixed in 80 µl of 0.5×TBE buffer (pH 6.5). The 40 mer dsDNAs used in the examples were as follows:

| Example | dsDNA |
|---------|-------|
| 1A | SEQ ID NO: 1 |
| 1B | SEQ ID NO: 2 |
| 1C | SEQ ID NO: 3 |
| 1D | SEQ ID NO: 4 |
| 1E | SEQ ID NO: 5 |

Each sample was heated at 95° C. for 5 minutes. Then, the samples were left to hybridize at room temperature for 20 minutes. Each sample was separated by G50 spin column (Pharmacia Biotech, Uppsala, Sweden) by spinning at 950 rpm for 3 minutes. The solution containing the hybridization complexes passed through the column and was transferred into a cuvette for fluorescent detection using the protocols disclosed in our prior U.S. patent applications Ser. Nos. 08/807,901, 08/870,370 and 08/886,280.

The detection results shown in FIG. 1 demonstrate that fluorescent intensity was inversely proportional to the number of mismatches between the probe and target. Thus, the perfectly matched target and probe of Example 1A fluoresced more intensely than the one base mismatch pair of Example 1B, which fluoresced more intensely than the two base mismatch pair of Example 1c, which fluoresced more intensely than the three base mismatch pair of Example 1D, which fluoresced more intensely than the untargeted DNA/probe pairing of Example 1E. The fluorescent spectra were recorded at an 800 ms integrating time.

Examples 2A–2E

In each of Examples 2A–2E, 40 pmol of 40 mer synthesized dsDNA was added to 50 pmol of methylphosphonate oligonucleotide probe 1 (SEQ ID NO:10) and mixed in 80 µl of 0.5×TBE buffer (pH 6.5). The 40 mer dsDNAs used in the examples were as follows:

| Example | dsDNA |
|---|---|
| 2A | SEQ ID NO: 1 |
| 2B | SEQ ID NO: 2 |
| 2C | SEQ ID NO: 3 |
| 2D | SEQ ID NO: 4 |
| 2E | SEQ ID NO: 5 |

Each sample was heated at 95° C. for 5 minutes. Then, the samples were left to hybridize at room temperature for 20 minutes. The solution containing the hybridization complexes was transferred into a cuvette for fluorescent detection, without separating unhybridized probe from the hybridization complexes.

Figure 2:
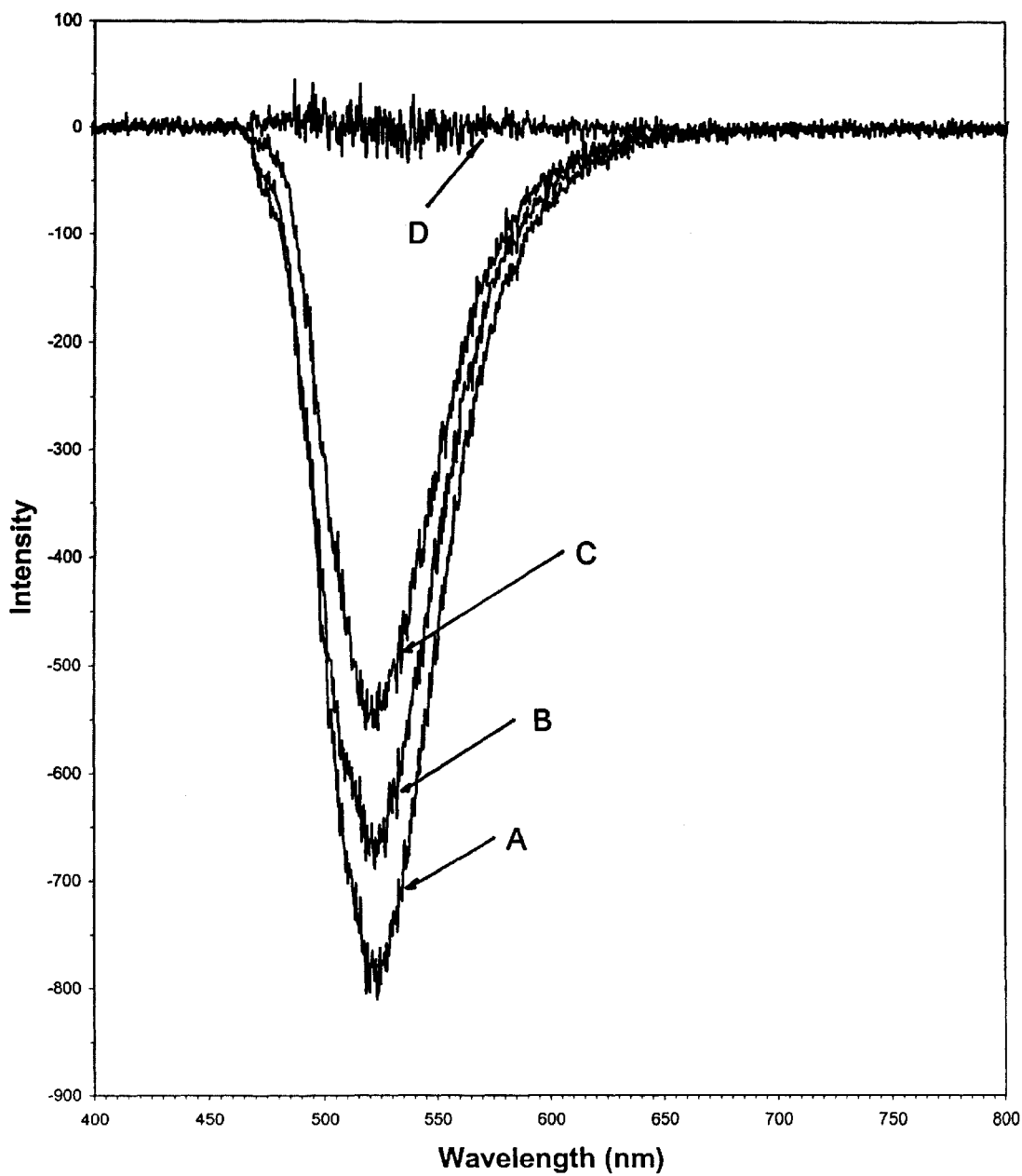
FIG. 2 shows the fluorescent quenching effect spectra resulting from assaying for several different targets and a non-target with 25% methylated DNA probes.

The resulting fluorescent intensity quenching spectra are shown in FIG. 2. The fluorescent spectrum of untargeted DNA (Example 2E) was used as a background or baseline spectrum and subtracted from all spectra. FIG. 2 shows that the intensity of the quenching effect is inversely proportional to the number of mismatches between the target and probe. The fluorescent spectra were recorded at a 200 ms integrating time.

Examples 3A–3D

In each of Examples 3A–3D, 8 pmol of 150 mer PCR dsDNA was added to 100 pmol of methylphosphonate oligonucleotide probe 1 (SEQ ID NO:10) and mixed in 80 μl of 0.5×TBE buffer (pH 6.5). The 150 mer dsDNAs used in the examples were as follows:

| Example | dsDNA |
|---|---|
| 3A | SEQ ID NO: 6 |
| 3B | SEQ ID NO: 7 |
| 3C | SEQ ID NO: 8 |
| 3D | SEQ ID NO: 9 |

Each sample was heated at 95° C. for 8 minutes. Then, the samples were left to hybridize at room temperature for 20 minutes. Each sample was separated by G50 spin column by spinning at 950 rpm for 3 minutes. The solution containing the hybridization complexes passed through the column and was transferred into a cuvette for fluorescent detection.

Figure 3:
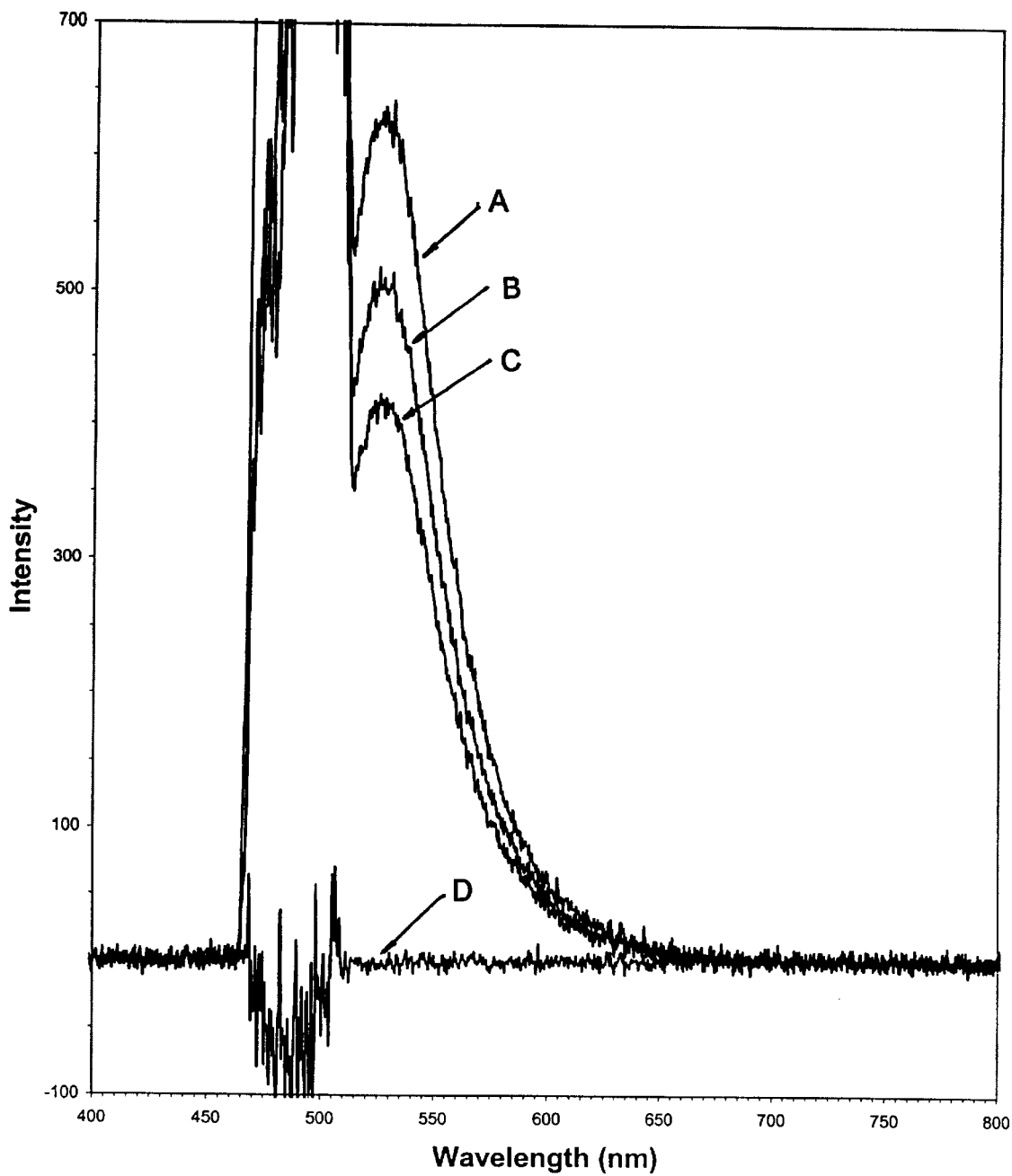
FIG. 3 shows the fluorescent spectra resulting from assaying for several different targets and a non-target with 25% methylated DNA probes.

The fluorescent spectrum of Example 3D was used as background spectrum and all spectra were recorded to subtract the background. FIG. 3 demonstrates that fluorescent intensity was inversely proportional with the number of mismatches between the probe and target. The largest intensity was obtained from the solution from the perfectly matched 150 bp PCR product and quarter-length methylated DNA probe (Example 3A), while the lowest intensity was obtained from the untargeted DNA example (Example 3D). The fluorescent spectra were recorded at a 2048 ms integrating time.

Example 4A–4D

In each of Examples 4A–4D, 8 pmol of 150 mer PCR dsDNA was added to 100 pmol of methylphosphonate oligonucleotide probe 2 (SEQ ID NO:11) and mixed in 80 μl of 0.5×TBE buffer (pH 6.5). The 150 mer dsDNAs used in the examples were as follows:

| Example | dsDNA |
|---|---|
| 4A | SEQ ID NO: 6 |
| 4B | SEQ ID NO: 7 |
| 4C | SEQ ID NO: 8 |
| 4D | SEQ ID NO: 9 |

Each sample was heated at 95° C. for 8 minutes. Then, the samples were left to hybridize at room temperature for 20 minutes. Each sample was separated by G50 spin column by spinning at 950 rpm for 3 minutes. The solution containing the hybridization complexes passed through the column and was transferred into a cuvette for fluorescent detection.

Figure 4:
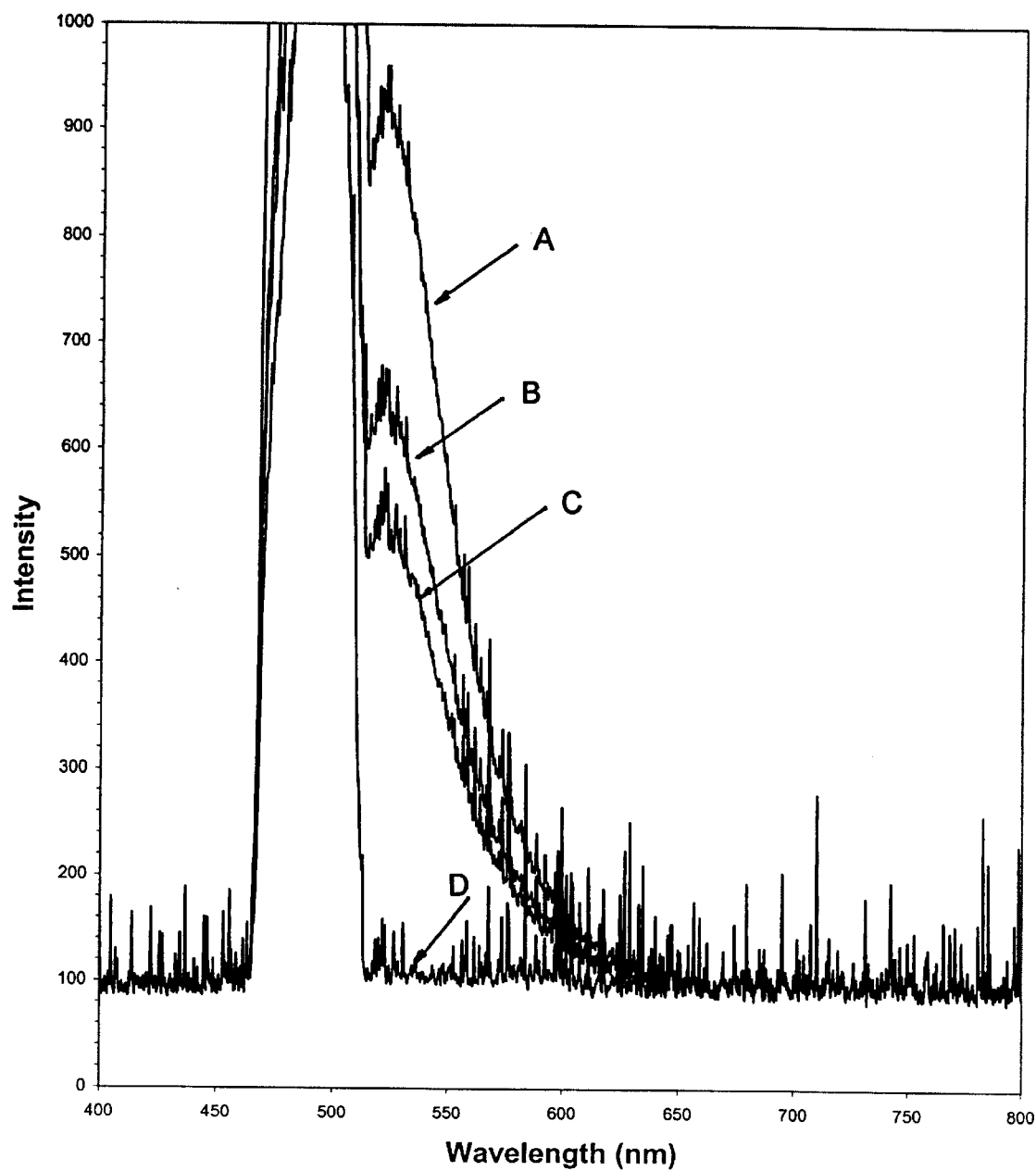
FIG. 4 shows the fluorescent spectra resulting from assaying for several different targets and a non-target with 50% methylated DNA probes.

The fluorescent spectrum of Example 4D was used as background spectrum and all spectra were recorded to subtract the background. FIG. 4 demonstrates that fluorescent intensity was inversely proportional with the number of mismatches between the probe and target. The largest intensity was obtained from the solution from the perfectly matched 150 bp PCR product and half-length methylated DNA probe (Example 4A), while the lowest intensity was obtained from the untargeted DNA example (Example 4D). The fluorescent spectra were recorded at a 2048 ms integrating time.

Examples 5A–5D

In each of Examples 5A–5D, 8 pmol of 150 mer PCR dsDNA was added to 100 pmol of methylphosphonate oligonucleotide probe 3 (SEQ ID NO:12) and mixed in 80 μl of 0.5×TBE buffer (pH 6.5). The 150 mer dsDNAs used in the examples were as follows:

| Example | dsDNA |
|---|---|
| 5A | SEQ ID NO: 6 |
| 5B | SEQ ID NO: 7 |
| 5C | SEQ ID NO: 8 |
| 5D | SEQ ID NO: 9 |

Each sample was heated at 95° C. for 8 minutes. Then, the samples were left to hybridize at room temperature for 20 minutes. Each sample was separated by G50 spin column by spinning at 950 rpm for 3 minutes. The solution containing the hybridization complexes passed through the column and was transferred into a cuvette for fluorescent detection.

Figure 5:
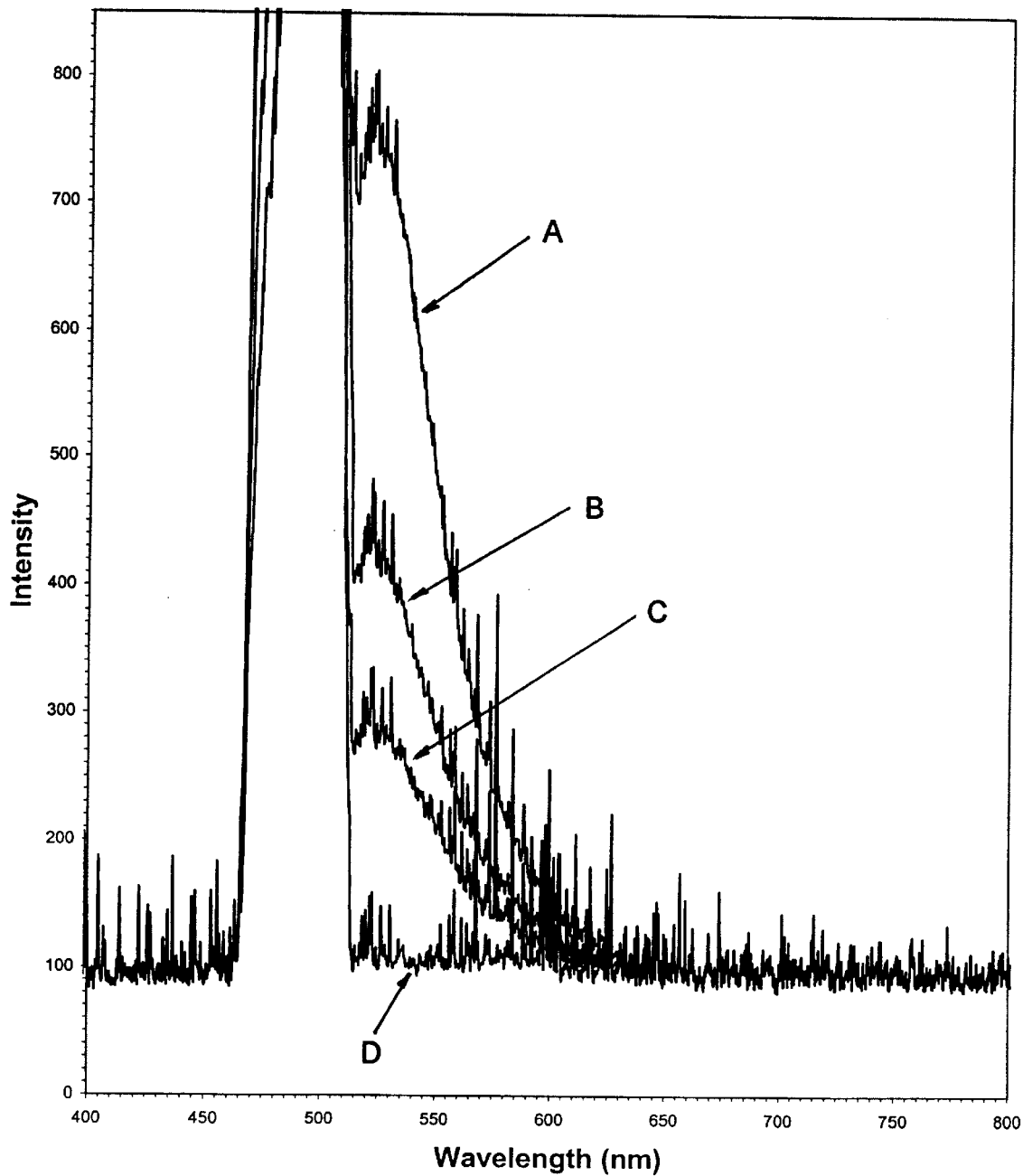
FIG. 5 shows the fluorescent spectra resulting from assaying for several different targets and a non-target with completely methylated, non-ionic, DNA probes.

The fluorescent spectrum of Example 5D was used as background spectrum and all spectra were recorded to subtract the background. FIG. 5 demonstrates that fluorescent intensity was inversely proportional with the number of mismatches between the probe and target. The largest intensity was obtained from the solution from the perfectly matched 150 bp PCR product and full-length methylated DNA probe (Example 5A), while the lowest intensity was obtained from the untargeted DNA example (Example 5D). The fluorescent spectra were recorded at a 2048 ms integrating time.

While the invention has been described in detail and with reference to specific examples thereof, it will be apparent to one skilled in the art that various changes and modifications can be made therein without departing from the spirit and scope thereof.

What is claimed is:

1. A method for detecting at least one single stranded or double stranded nucleobase-containing target sequence in a fluid medium, said method comprising:

adding to said fluid medium antisense probes capable of forming hybridization complexes with said at least one nucleobase-containing target sequence, wherein said antisense probes comprise a backbone having a charge that is less negative than a comparable phosphodiester backbone;

separating unhybridized antisense probes from said hybridization complexes to form a test medium;

irradiating said test medium with a laser beam having a wavelength which excites fluorescent markers in said hybridization complexes and causes said fluorescent markers to emit fluorescent light;

measuring an intensity of said emitted fluorescent light; and comparing said measured intensity with a reference intensity to detect whether said fluid medium contains said at least one target sequence, wherein an inverse of said measured intensity is proportional to a number of base mismatches between said at least one nucleobase-containing target sequence and said antisense probes, over a range inclusive of 0 base mismatches through at least 3 base mismatches, and wherein said method other than said separating step is entirely conducted without binding said antisense probes, said at least one nucleobase-containing target sequence or said hybridization complex to a solid support or gel.

2. The method of claim 1, wherein said backbone comprises at least one non-ionic linking group between a 5' carbon and a 3' carbon of adjacent sugars.

3. The method of claim 2, wherein said at least one non-ionic linking group is a methylphosphonate group.

4. The method of claim 1, wherein said backbone comprises a modified phosphodiester backbone having at least about 10% of its phosphate groups replaced with non-ionic groups.

5. The method of claim 4, wherein said non-ionic groups are methylphosphonate groups.

6. The method of claim 1, wherein said backbone comprises a modified phosphodiester backbone having at least about 20% and not more than about 80% of its phosphate groups replaced with non-ionic groups.

7. The method of claim 6, wherein said non-ionic groups are methylphosphonate groups.

8. The method of claim 1, wherein said backbone comprises a modified phosphodiester backbone having about 25% of its phosphate groups replaced with non-ionic groups.

9. The method of claim 8, wherein said non-ionic groups are methylphosphonate groups.

10. The method of claim 1, wherein said backbone comprises a modified phosphodiester backbone having about 50% of its phosphate groups replaced with non-ionic groups.

11. The method of claim 10, wherein said non-ionic groups are methylphosphonate groups.

12. The method of claim 1, wherein said backbone comprises at least one peptide segment and at least one phosphodiester segment.

13. The method of claim 1, wherein said backbone comprises at least one peptide segment and at least one methylphosphonate segment.

14. A method for detecting at least one single stranded or double stranded nucleobase-containing target sequence in a fluid medium, said method comprising:

adding to said fluid medium antisense probes capable of forming a hybridization complex with said at least one nucleobase-containing target sequence, wherein said antisense probes comprise a backbone having a charge that is less negative than a comparable phosphodiester backbone;

irradiating said fluid medium with a laser beam having a wavelength which excites fluorescent markers in said hybridization complex and causes said fluorescent markers to emit fluorescent light;

measuring an intensity of said emitted fluorescent light; and comparing said measured intensity with a reference intensity to detect whether said fluid medium contains said at least one target sequence, wherein said measured intensity is proportional to a number of base mismatches between said at least one nucleobase-containing target sequence and said antisense probes, over a range inclusive of 0 base mismatches through at least 3 base mismatches, and wherein said method is conducted without separating unhybridized probes from hybridization complexes prior to said signal detecting, and without providing a signal quenching agent on said antisense probes or on said at least one nucleobase-containing target sequence.

15. The method of claim 14, wherein said measured intensity is inversely proportional to an amount of hybridization complexes in said fluid medium and proportional to an amount of said antisense probes unhybridized in said fluid medium.

16. The method of claim 14, wherein said backbone comprises at least one non-ionic linking group between a 5' carbon and a 3' carbon of adjacent sugars.

17. The method of claim 16, wherein said at least one non-ionic linking group is a methylphosphonate group.

18. The method of claim 14, wherein said backbone comprises a modified phosphodiester backbone having at least about 10% of its phosphate groups replaced with non-ionic groups.

19. The method of claim 18, wherein said non-ionic groups are methylphosphonate groups.

20. The method of claim 14, wherein said backbone comprises a modified phosphodiester backbone having at least about 20% and not more than about 80% of its phosphate groups replaced with non-ionic groups.

21. The method of claim 20, wherein said non-ionic groups are methylphosphonate groups.

22. The method of claim 14, wherein said backbone comprises a modified phosphodiester backbone having about 25% of its phosphate groups replaced with non-ionic groups.

23. The method of claim 22, wherein said non-ionic groups are methylphosphonate groups.

24. The method of claim 14, wherein said backbone comprises a modified phosphodiester backbone having about 50% of its phosphate groups replaced with non-ionic groups.

25. The method of claim 24, wherein said non-ionic groups are methylphosphonate groups.

26. The method of claim 14, wherein said backbone comprises at least one peptide segment and at least one phosphodiester segment.

27. The method of claim 14, wherein said backbone comprises at least one peptide segment and at least one methylphosphonate segment.

28. The method of claim 1, wherein said at least one nucleobase-containing target sequence is a first segment within a folded nucleotide sequence, and said measured intensity is compared with a second measured intensity of a second segment within said folded nucleotide sequence to identify antisense probe accessible regions in said folded nucleotide sequence.

29. The method of claim 14, wherein said at least one nucleobase-containing target sequence is a first segment within a folded nucleotide sequence, and said measured intensity is compared with a second measured intensity of a second segment within said folded nucleotide sequence to identify antisense probe accessible regions in said folded nucleotide sequence.

30. The method of claim 1, wherein the number of base mismatches between said at least one nucleobase-containing target sequence and said antisense probes is determined.

31. The method of claim 14, wherein the number of base mismatches between said at least one nucleobase-containing target sequence and said antisense probes is determined.

* * * * *